United States Patent
Werner (10) Patent No.: US 9,131,678 B1
(45) Date of Patent: Sep. 15, 2015

(54) ULTRAVIOLET STRATEGY FOR AVIAN REPELLENCY

(71) Applicant: The United States of America, as represented by the Secretary of Agriculture, Washington, DC (US)

(72) Inventor: Scott J. Werner, Wellington, CO (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 42 days.

(21) Appl. No.: 13/755,671

(22) Filed: Jan. 31, 2013

Related U.S. Application Data (63) Continuation-in-part of application No. 12/652,944, filed on Jan. 6, 2010.

(60) Provisional application No. 61/143,215, filed on Jan. 8, 2009.

(51) Int. Cl.
*A01N 25/00* (2006.01)
*A01N 35/06* (2006.01)

(52) U.S. Cl.
CPC ............... *A01N 25/00* (2013.01); *A01N 35/06* (2013.01)

(58) Field of Classification Search
CPC .................................... C07C 2/22; C07F 9/02
USPC .......................................... 424/405; 427/160
See application file for complete search history.

(56) References Cited

U.S. PATENT DOCUMENTS

2005/0186237 A1* 8/2005 Day et al. ...................... 424/405
2008/0207446 A1* 8/2008 Gerber et al. ................. 504/100

OTHER PUBLICATIONS

Werner, Scott J., et al., "Anthraquinone repellent to reduce take of non-target birds from zinc phosphide rodenticide applications", Applied Animal Behavior Science, 135, 2011, pp. 146-153.
Werner, Scott J., et al., "Threshold concentrations of an anthraquinone-based repellent for Canada geese, red-winged blackbirds, and ring-necked pheasants", Applied Animal Behaviour Science, 121, 2009, pp. 190-196.
Werner, Scott J., et al., "The role of a generalized ultraviolet cue for blackbird food selection", Physiology and Behavior, 106, 2012, pp. 597-601.
Werner, Scott J., et al., "Reconciling sensory cues and varied consequences of avian repellents", Physiology & Behavior, 102, 2011, pp. 158-163.

* cited by examiner

*Primary Examiner* — Janet Epps Smith
*Assistant Examiner* — Courtney Brown
(74) *Attorney, Agent, or Firm* — John D. Fado; Robert D. Jones; Lesley Shaw (57) ABSTRACT

By using visual cue agents that exhibit spectral characteristics sufficiently similar to a previously-applied repellent treatment, the amount of the repellent agents used in subsequent or repeat applications may be significantly reduced while still effectively repelling birds. The method for repelling birds from a target includes the application of a first treatment of a bird repellent agent to the target in an amount effective to repel the birds of interest. Subsequently, one or more additional treatment(s) is/are applied to the target including a visual cue agent that exhibits an ultraviolet absorbance spectrum or color which is sufficiently similar to the previously-applied repellent treatment. In these subsequent applications, the bird repellent agent may be applied at a significantly lower amount than the first treatment.

14 Claims, 5 Drawing Sheets

ULTRAVIOLET STRATEGY FOR AVIAN REPELLENCY

CROSS-REFERENCE TO RELATED APPLICATION

This application is a continuation-in-part of U.S. patent application Ser. No. 12/652,944, filed on Jan. 6, 2010, which claims the benefit under 35 U.S.C. 1.19(e) of U.S. provisional No. 61/143,215, filed Jan. 8, 2009, the contents of each of which are incorporated by reference herein.

BACKGROUND OF THE INVENTION

1. Field of the Invention

The invention relates to compositions and methods for repelling wild birds from target foods or places.

2. Description of the Prior Art

Several bird species cause monetary losses to agricultural production throughout the United States. For example, red-winged blackbirds (*Agelaius phoeniceus*), common grackles (*Quiscalus quiscula*), and brown-headed cowbirds (*Molothrus ater*) caused approximately US $13.4 million of damage to United States rice production in 2001 (Cummings et al. 2005, Economic impacts of blackbird damage to the rice industry. Wildlife Damage Management Conference. 11:317-322). Significant economic losses due to birds are also incurred in a number of other crops, including, but not limited to corn, fruit, grains, grasses, legumes, lettuce, millet, oats, rice, row crops, sorghum, sunflower, tree nuts, turf, vegetables, and wheat. Efforts to manage damages to rice and other crops have included the use of a variety of repellents and other nonlethal management alternatives (Werner et al. 2005, Evaluation of Bird Shield™ as a blackbird repellent in ripening rice and sunflower fields. Wildlife Society Bulletin. 33: 251-257). For example, chemical repellents can be used as seed treatments to reduce bird impacts to newly planted crops or as aerial applications to reduce bird consumption of ripening crops.

Methyl and dimethyl anthranilate (MA and DMA, respectively) are ester derivatives of anthranilic acid (also known as orthoamino-benzoic acid). MA, DMA and other derivatives of anthranilic acid as well as esters of phenylacetic acid, are known to be bird aversion agents with preferred embodiments as feed additives to deter feed loss (U.S. Pat. Nos. 2,967,128 and 4,790,990), and as an anti-grazing compound for geese and swans (Mason, J. R. et al., "Anthranilate Repellency to Starlings: Chemical Correlates and Sensory Perception", JOURNAL OF WILDLIFE MANAGEMENT, 53:55-64 (1989)). Cinnamamide has also been shown to be a bird aversion agent (Crocker & Perry, PLANT CHEMISTRY AND BIRD REPELLENTS, 132: 300-308 (1990)).

U.S. Pat. No. 2,967,128 discloses the incorporation of MA and other ester derivatives of anthranilic acid as bird aversion agents into feed or pesticide additives, or into liquids to be sprayed on material. U.S. Pat. No. 4,790,990 teaches that the aversion agent can be at least partially trapped in a solid vehicle to improve its persistency. The solid vehicle can be a modified starch, oil or polymer which microencapsulates the aversion agent.

Schafer et al. (1983, The acute oral toxicity, repellency, and hazard potential of 998 chemicals to one or more species of wild and domestic birds. Archives of Environmental Contamination and Toxicology. 12:355-382) identified caffeine as a potential avian repellent with relatively low toxicity ($LD50$=316 mg/kg for European starlings [*Sturnus vulgaris*]). Avery and Cummings (2003, Chemical repellents for reducing crop damage by blackbirds. Pages 41-48 in Linz G. M. Proceedings of the management of North American blackbirds symposium. The Wildlife Society Ninth Annual Conference, 27 Sep. 2002, Bismarck, N. Dak., USA) found that 2,500 ppm caffeine reduced rice consumption by 76% among male red-winged blackbirds in captivity. Blackbirds consumed <10% of rice seeds treated with 10,000 ppm caffeine and >80% of untreated rice seeds under field conditions in southwestern Louisiana, USA (Avery et al. 2005, Caffeine for reducing bird damage to newly seeded rice. Crop Protection. 24: 651-657).

To extend the effectiveness of some repellents, repellent agents have been combined with visual cues or colors. These visual cues or colors serve as preingestive warnings to birds. Birds readily learn to associate these visual cues with unpleasant feeding experiences [Mason, Direct and observational avoidance learning by red-winged blackbirds (*Agelaius phoeniceus*): the importance of complex visual stimuli. In: T. Zentall and B. G. Galef, Editors, Social Learning: A Biopsychological Approach, Lawrence Erlbaum, Hillsdale, N.J. (1988), pp. 99-115].

While tastes are likely the most potent conditional stimuli in the process of mammalian food consumption [Garcia, Food for Tolman: cognition and cathexis in concert. In: T. Archer and L. Nilsson, Editors, Aversion, avoidance and anxiety, Erlbaum, Hillsdale (1989), pp. 45-85], food preference among bobwhite quail (*Colinus virginianus*) is affected by the color of food, and visual stimuli can actually overshadow salient tastes upon conditioning illness-induced aversions [Wilcoxon et al. 1971, Illness-induced aversions in rat and quail: relative salience of visual and gustatory cues, Science, 171:826-828]. Food aversions can be reliably conditioned in red-winged blackbirds (*Agelaius phoeniceus*) using toxic gavage (methiocarb and lithium chloride) paired with colored oats [Mason and Reidinger, 1983, Importance of color for methiocarb-induced food aversions in red-winged blackbirds, J Wildl Manage, 47:383-393]: oats colored differently from the color paired with LiCl were preferred through 4 weeks of post-treatment testing. Furthermore, conspecifics that observed aversive conditioning events similarly formed aversions to colors paired with toxicosis, even though they did not ingest the toxin themselves [Mason et al. 1984, Comparative assessment of food references and aversions acquired by blackbirds via observational learning, Auk, 101: 796-803]. Similarly, quelea (*Quelea quelea*) [Elmandi et al. 1985, Calcium carbonate enhancement of methiocarb repellency for *quelea*, Trop Pest Manage, 31:67-72] and eared doves (*Zenaida auriculata*) [Rodriguez et al. An integrated strategy to decrease eared dove damage in sunflower crops. In: J. R. Mason, Editor, Repellents in wildlife management: proceedings of a symposium, National Wildlife Research Center, Fort Collins (1997), pp. 409-421] avoided calcium carbonate-treated crops when presence of the white powder was associated with methiocarb-induced toxicosis. Thus, at least for granivorous birds, color may be the dominant cognitive cue during the food consumption process and visual stimuli may enhance the efficacy of chemical repellents used to reduce bird damage to agricultural production [Avery and Mason, 1997, Feeding responses of red-winged blackbirds to multisensory repellents, Crop Prot, 16:159-164] and [Nelms and Avery, 1997, Reducing bird repellent application rates by the addition of sensory stimuli, Int J Pest Manage, 43:187-190].

However, despite these and other advances, the need remains for an improved system for repelling birds. Chemical repellent applications are typically constrained by a variety of factors, including cost, environmental effects, and food and feed safety. Thus, effective long-term repellence of birds from a target (i.e., food or place) typically requires repeated applications of the chemical repellents. However, repeated applications not only drive up costs, but such repeat applications may be limited to legally permissible aggregate concentrations of the repellent agent per season.

SUMMARY OF THE INVENTION

I have discovered improved compositions and methods for repelling birds using bird repellent agents in combination with visual cue agents. By using visual cue agents that exhibit spectral characteristics sufficiently similar to the previously-applied repellent treatment that the birds do not visibly differentiate between the treatments, the amount of the repellent agent may be significantly reduced and yet effectively repel birds. The method of this invention for repelling birds from a target comprises the application of a first treatment of a bird repellent agent to the target in an amount effective to repel the birds of interest. Subsequently, one or more additional treatment(s) is/are applied to the target including a visual cue agent that exhibits spectral characteristics sufficiently similar to the previously-applied repellent treatment. In these subsequent applications, the bird repellent agent may be omitted or applied at a significantly lower amount than the first treatment, and the visual cue agent is applied at an amount effective to be visibly recognized by the birds.

In accordance with this discovery, it is an object of this invention to provide improved methods and compositions for repelling birds from a target.

Another object of this invention is to provide improved methods and compositions for repelling birds using significantly reduced amounts of bird repellent agents applied throughout the period of needed repellency.

A further object of this invention is to provide improved methods and compositions for repelling birds utilizing multiple applications of bird repellent agents wherein the amount of the repellent agents may be significantly reduced after the initial application.

Other objects and advantages of this invention will become readily apparent from the ensuing description.

BRIEF DESCRIPTION OF THE DRAWINGS

FIG. 4 illustrates test consumption among individually-caged birds subsequent to repellent conditioning (Example 2). Conditioning groups 1-3 received one bowl of sunflower seeds treated with an ultraviolet-absorbent cue (control group), an anthraquinone-based repellent (anthraquinone conditioning group), or an methyl anthranilate-based repellent (methyl anthranilate conditioning group); all birds were also gavaged with 2 g of sunflower seeds treated in accordance with their conditioning group during the 1-day conditioning period to ensure preingestive cue/postingestive consequence conditioning. All birds (groups 1-3) were subsequently offered sunflower seeds treated only with the ultraviolet-absorbent cue during a 4-day test. Sunflower consumption among birds conditioned with the anthraquinone- or methyl anthranilate-based repellents was significantly less than that exhibited among birds in the control group (P<0.001).

DETAILED DESCRIPTION OF THE INVENTION

In contrast to the visual cues described in the prior art which are distinct colors (i.e., different from the repellent agent) that the birds learn to associate with a negative response (caused by the co-applied repellent agent) and therefore avoid, the visual cues of this invention exhibit spectral characteristics sufficiently similar to the previously-applied repellent treatment that the birds do not visibly differentiate between the two agents or treatments. The combined use of the visual cue of this invention with the repellent agent allows the concentration of the repellent agent to be reduced subsequent to the first application (Werner et al. 2008, Food color, flavor, and conditioned avoidance among red-winged blackbirds. Physiology & Behavior. 93: 110-117, the contents of which are incorporated by reference herein).

The methods and compositions of the invention are effective for repelling a variety of birds from any target (i.e., food or place) of interest. The invention is preferably used for repelling wild birds, including but not limited to, blackbird species (*Icteridae*), including red-winged blackbirds (*Agelaius phoeniceus*), grackles (*Quiscalus* spp.), yellow-headed blackbirds (*Xanthocephalus xanthocephalus*), and brown-headed cowbirds (*Molothrus ater*); starlings, including European starlings (*Sturnus vulgaris*); geese, including Canada geese (*Branta canadensis*), cackling geese (*B. hutchinsii*), and snow geese (*Chen caerulescens*); crows, cranes, swans, pheasants, wild turkeys, pigeons, sparrows, woodpeckers, larks, robins, finches, and waxwings.

Bird repellent agents which are suitable for use in the invention are those that are efficacious as primary and/or secondary repellents. Primary repellents possess a quality (e.g., unpalatable taste, odor, irritation) that evokes reflexive withdrawal or escape behavior in an animal. In contrast, secondary repellents evoke an adverse physiological effect (e.g., illness, pain), which in turn is associated with a subsequently-avoided sensory stimulus (e.g., taste, odor, visual cue; Werner & Clark 2003, Understanding blackbird sensory systems and how repellent applications work. In: Linz, G. M., ed. Management of North American Blackbirds. Washington, D.C.: United States Department of Agriculture; p31-40).

A variety of bird repellents have been previously described and are suitable for use herein, and include but are not limited to anthraquinones, flutolanil, anthranilates (including methyl and dimethyl anthranilate), methiocarb, caffeine, chlorpyrifos, (plus-cyhalothrin), methyl phenyl acetate, ethyl phenyl acetate, o-amino acerophenone, 2-amino-4,5-dimethyl ecetophenone, veratroyl amine, cinnamic aldehyde, cinnamic acid, cinnamide, and chitosan. These agents may be used alone or in combination. Similarly, the techniques for application of these agents are also well-known and have been described, including formulations, application rates, and application techniques. See, for example, Hermann (U.S. Pat. No. 3,941,887) describing the use of anthraquinones, Wilson (published U.S. application 2007/0178127 A1) describing the use of flutolanil, Kare (U.S. Pat. No. 2,967,128) and Mason (U.S. Pat. No. 4,790,990) describing the use of anthranilates and esters of phenyl acetic acid, Crocker and Perry (1990, ibid) describing the use of cinnamide, Schafer et al. (1983, ibid) and Werner et al. (2005, Caffeine Formulation for Avian Repellency. J Wildlife Management, 71:1676-1681) describing the use of caffeine and caffeine plus benzoate, respectively, and Preiser (U.S. Pat. No. 5,549,902) describing the use of any of anthranilates, methyl phenyl acetate, ethyl phenyl acetate, o-amino acerophenone, 2-amino-4,5-dimethyl ecetophenone, veratroyl amine, cinnamic aldehyde, cinnamic acid or cinnamide, the contents of each of which citations are incorporated by reference herein. Many formulations of these repellents are also available commercially, including but not limited to, 9,10-anthraquinone (AVIPEL, FLIGHT CONTROL PLUS, AV-1011, and AV-2022, all marketed by Arkion Life Sciences, New Castle, Del.), flutolanil (GWN-4770 and GWN-4771, marketed by the Gowan Company, Yuma, Ariz.), methyl anthranilate (BIRD SHIELD, marketed by the Bird Shield repellent Corp., Spokane, Wash.), methiocarb (MESUROL, marketed by the Gowan Company, Yuma, Ariz.), caffeine (Flavine North America, Inc., Closter, N.J.), and chlorpyrifos (plus-cyhalothrin; COBALT, marketed by Dow AgroSciences, Indianapolis, Ind.).

As noted hereinabove, suitable visual cue agents of this invention exhibit spectral characteristics sufficiently similar to the previously-applied repellent treatment that the birds of interest do not visually differentiate between the visual cue agent and the bird repellent agent or the first treatment formulation containing the repellent agent. For example, by way of illustration and without being limited thereto, the preferred bird repellents, anthraquinone, flutolanil, anthranilate, methiocarb, caffeine, and chlorpyrifos (plus-cyhalothrin) all exhibit UV-A (320-400 nm) and/or UV-B (280-320 nm) absorbance. Thus, suitable visual cue agents should exhibit ultraviolet absorbance at or sufficiently near these wavelengths. A variety of visual cue agents are suitable for use herein, and may be identified by determination of the UV absorption spectra of the bird repellent agent of interest (or the formulation of the first treatment in which the repellent agent is applied) and candidate UV absorbing compounds or agents, and selecting as visual cue agents those UV absorbing agents which possess a UV absorbance spectrum or color that is substantially the same as that of the bird repellent agent or the first treatment. The UV absorption spectra of other bird repellent agents and visual cue agents may be readily determined using conventional spectroscopic analysis techniques. Although the visual cue agent may itself be effective as a repellent, typically, the visual cue agents will exhibit no statistically significant level of repelling or attracting unconditioned birds when used alone. Preferred visual cue agents for use herein, include, but are not limited to, titanium (IV) oxides ($TiO_2$), trisiloxanes, siloxanes, and other UV-B- and/or UV-A-absorbent agents.

The amount of the bird repellent agent used will vary from the initial to the subsequent applications. In the initial application (as well as any subsequent applications in the absence of visual cue agent), the amount of the repellent agent is selected to effectively repel birds from a treated target (i.e., food or place). Thus, as used herein, an "effective amount" is defined as that amount which results in a significant repellence of the birds from a treated target in comparison to an untreated control (target without repellent). The actual effective amount will vary with the particular repellent agent selected, its formulation, the bird pest, the target, and environmental factors, and may be readily determined by routine controlled experimentation. Suitable amounts and formulations are described in the prior art as noted hereinabove, and are also provided by the repellent manufacturers and suppliers. By way of example and without being limited thereto, in the initial application, preferred amounts of anthroquinone (AVIPEL, FLIGHT CONTROL PLUS, AV-1011 or AV-2022) are approximately 2,000 ppm active ingredient (a.i.) for most birds, but may be as low as 600 ppm a.i. for larks, preferred amounts of flutolanil are 35,000 ppm (GWN-4770) or 15,000 ppm (GWN-4771), preferred amounts of anthranilate (BIRD SHIELD) are 80,000 ppm a.i., preferred amounts of methiocarb (MESUROL 75-W) vary from 1,250 ppm a.i. for blackbirds to 30 ppm a.i. for larks and 15 ppm a.i. for robins, starlings, grackles, finches, and waxwings, preferred amounts of caffeine (1:1 caffeine plus sodium benzoate) are 3,500 ppm a.i., and preferred amounts of chlorpyrifos plus (-cyhalothrin (COBALT) are 2,500 ppm a.i. It is also understood that while the visual cue agent may be applied with the initial repellent application, its application at this time provides no advantage and may be omitted until the subsequent applications.

Figure 5:
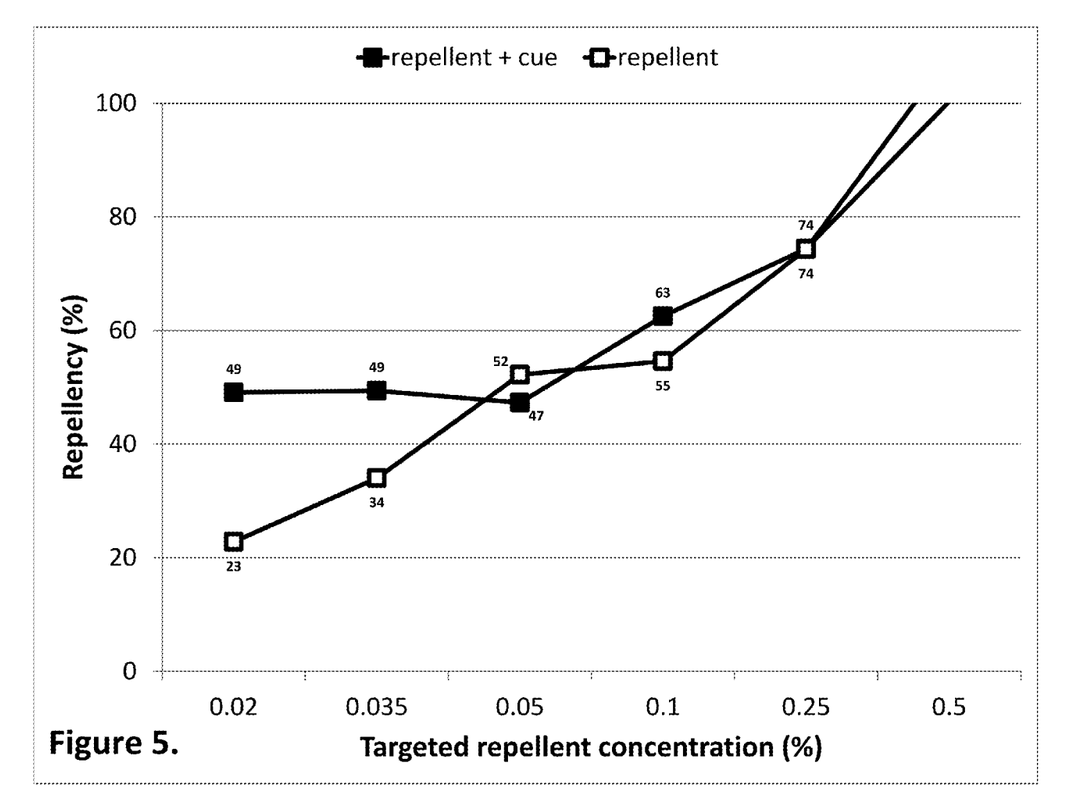
FIG. 5 comparatively illustrates avian repellency of food treated with 0.02-0.5% of the repellent and 0.2% of the ultraviolet cue ("repellent+cue") and food treated only with 0.02-0.5% of the repellent ("repellent") as described in Example 3. Repellency of the "repellent+cue" treatment was 49% for the 0.02% and 0.035% targeted repellent concentrations; in contrast, repellency of the "repellent" treatment was only 23% and 34% for the 0.02% and 0.035% targeted repellent concentrations, respectively. Whereas the ultraviolet cue itself is not repellent to tested birds (Example 1; Werner et al. 2012, The role of a generalized ultraviolet cue for blackbird food selection. Physiology & Behavior. 106:597-601), a synergistic repellency manifests from the addition of the ultraviolet cue to relatively low concentrations of the repellent food treatment.

In the subsequent applications wherein the bird repellent agent is applied in conjunction with the visual cue agent, the amount of the repellent agent is significantly reduced. In these later applications, suitable amounts of the repellent agent may be between about 2% to about 60% of the amount used in the initial application, preferably between about 10% to about 60% of the amount used in the initial application, more preferably between about 25% to about 60% of the amount used in the initial application, and most preferably between about 40% to about 60% of the amount used in the initial application. We have also unexpectedly discovered that in applications wherein the amount of the repellant agent is greatly reduced, that is, to less than 10% of the amount used in the initial application, particularly between 4% to 9%, and most preferably between 4% to 7%, a synergistic increase in repellency is observed upon addition of visual cue agent as demonstrated in Example 3. However, the overall efficacy, as measured by % repellency, remains less than that of formulations containing high levels of repellant agent (FIG. 5). The amount of the efficacious visual cue agent applied can be readily determined by routine controlled experimentation. The amount will also vary with the particular visual agent, its formulation, and the target. By way of example and without being limited thereto, preferred amounts of titanium (IV) oxide may vary from 2,000 to 5,000 ppm (AEROXIDE P25, Evonik Goldschmidt Corp., Hopewell, Va.) to 3,500 to 5,000 ppm (Catalog no. 232033 available from Aldrich, St. Louis, Mo.) to 4,000 to 7,000 ppm (Catalog no. 808 available from Merck & Co., Whitehouse Station, N.J.; HOMBIKAT UV 100 available from Sachtleben, Duisburg, Germany; Catalog no. 89490 available from Aldrich, St. Louis, Mo.; Catalog no.

T315-500 available from Fisher Scientific, Pittsburgh, Pa.). Preferred amounts of trisiloxane may vary from 300 to 500 ppm, and siloxane may vary from 3,500 to 5,000 ppm.

As a practical matter, it is anticipated that the bird repellent agent will be formulated with a suitable inert carrier as is known in the art. Formulations of the bird repellent agent and the visual cue agent may vary with the particular target and method of application. The agents may, for example, be formulated as solutions, emulsions, emulsifiable concentrates, suspension concentrates, wettable powders, dusts, granules, adherent dusts or granules, and aerosols. Of greatest interest are those carriers which are agronomically acceptable and those suitable for application onto structures, agricultural fields or crops, seeds, seedlings, orchards, vineyards, livestock feed, fertilizers, pesticides, animal or insect baits, and combinations thereof. The particular carrier selected is not critical, and a variety of liquid and solid phase carriers may be used, including but not limited to water, aqueous surfactant mixtures, alcohols, ethers, hydrocarbons, halogenated hydrocarbons, glycols, ketones, esters, oils (natural or synthetic), clays, kaolinite, silicas, cellulose, rubber, talc, vermiculate, and synthetic polymers. The bird repellent agent and the visual cue agent may also be formulated in a single composition or formulated in different compositions and applied separately. The repellent agent and/or the visual cue agent may also be formulated in admixture with other agriculturally beneficial agents, including but not limited to, ultraviolet stabilizers, antioxidants, baits, adjuvants, herbicidal agents, fertilizers, and pesticides including insecticides and fungicides.

The method of the invention may be used to repel birds anywhere they pose a nuisance or, more importantly, to prevent or minimize economic damage, particularly to agricultural products. The repellent agent and the visual cue agent may be applied on any target or spatial location of concern from which birds are to be repelled. In accordance with this invention, preferred targets for application include, but are not limited to, one or more of structures, agricultural fields or crops, seeds, seedlings, orchards, vineyards, livestock feed, fertilizers, pesticides, animal or insect baits, and combinations thereof. Crops include, but are not limited to, one or more of corn, fruit, grains, grasses, legumes, lettuce, millet, oats, rice, row crops, sorghum, sunflower, tree nuts, turf, vegetables, and wheat.

The subsequent treatments of the target with the repellent agent and the visual cue agent are typically applied at any time following the initial application desired by the user. For instance, in one anticipated embodiment, the subsequent treatments are applied when the efficacy of the initial application is significantly reduced or during periods wherein heavier bird damage is anticipated. In practice, the subsequent treatment is typically applied at least one week after the first treatment (in the same growing season).

The following example is intended only to further illustrate the invention and is not intended to limit the scope of the invention which is defined by the claims.

Example 1

Figure 1:
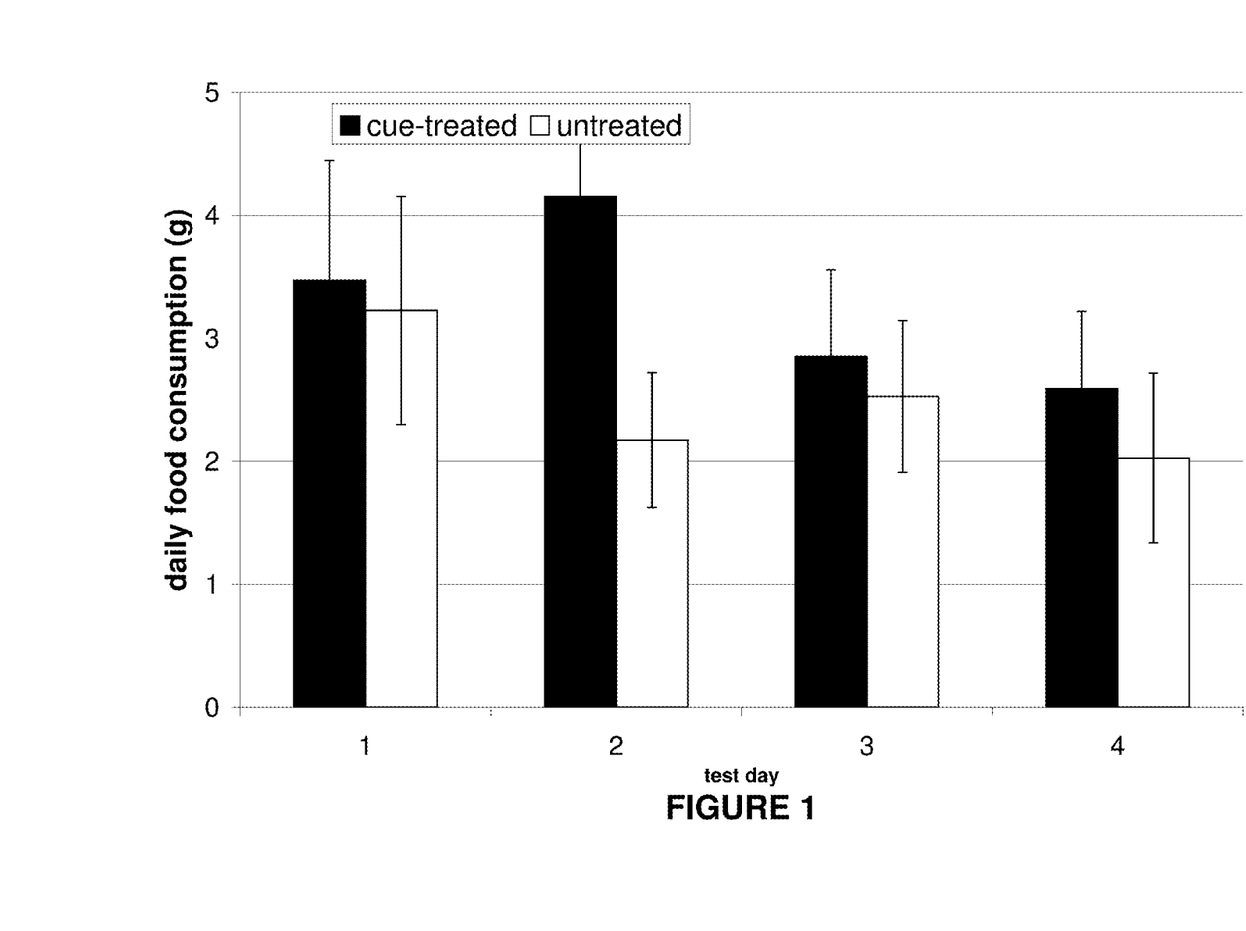
FIG. 1 illustrates baseline preference of individually-caged birds for treated (i.e., ultraviolet-absorbent cue) versus untreated food (Example 1). Baseline results indicate preferences independent of repellent consequences. Consumption of treated and untreated food did not differ among 11 birds during the 4-day test (P=0.234).

In the first of three experiments, 11 red-winged blackbirds were offered one bowl of sunflower seeds treated with an ultraviolet-absorbent cue ($TiO_2$, AEROXIDE P25, Evonik Goldschmidt Corp., Hopewell, Va.) and one bowl of untreated sunflower seeds within individual cages. Daily food consumption was measured. This baseline (i.e., control) experiment evaluated preferences independent of repellent conditioning for individually-caged birds. Consumption of treated and untreated food did not differ during the 4-day test (P=0.234; FIG. 1).

Figure 2:
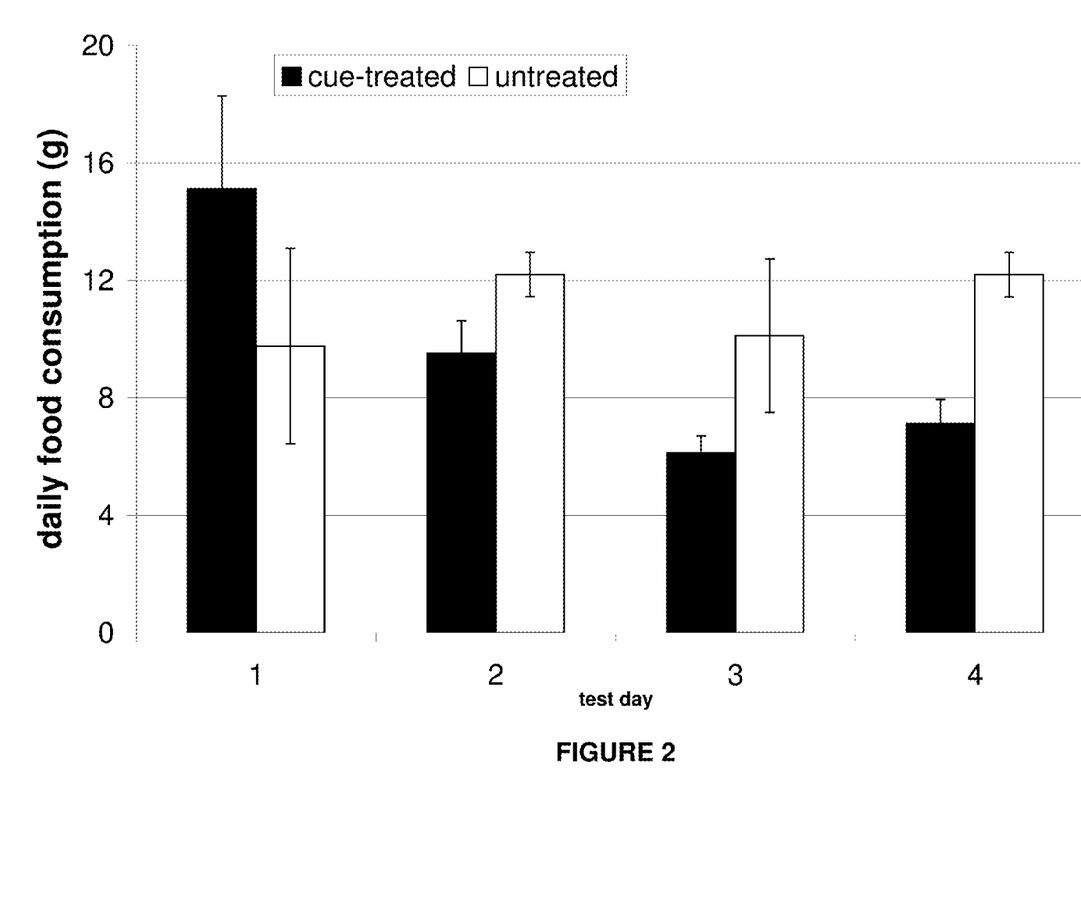
FIG. 2 illustrates baseline preference of group-caged birds for treated (i.e., ultraviolet-absorbent cue) versus untreated food (Example 1). Baseline results indicate preferences independent of repellent consequences. Consumption of treated and untreated food did not differ among 5 cages of birds (5 birds per cage) during the 4-day test (P=0.419).

In the second of three experiments, 5 red-winged blackbirds within each of 5 cages were offered one bowl of sunflower seeds treated with an ultraviolet-absorbent cue (AEROXIDE P25, Evonik Goldschmidt Corp., Hopewell, Va.) and one bowl of untreated sunflower seeds. Daily food consumption was again measured. This baseline (i.e., control) experiment evaluated preferences independent of repellent conditioning for group-caged birds. Consumption of treated and untreated food did not differ during the 4-day test (P=0.419; FIG. 2).

Figure 3:
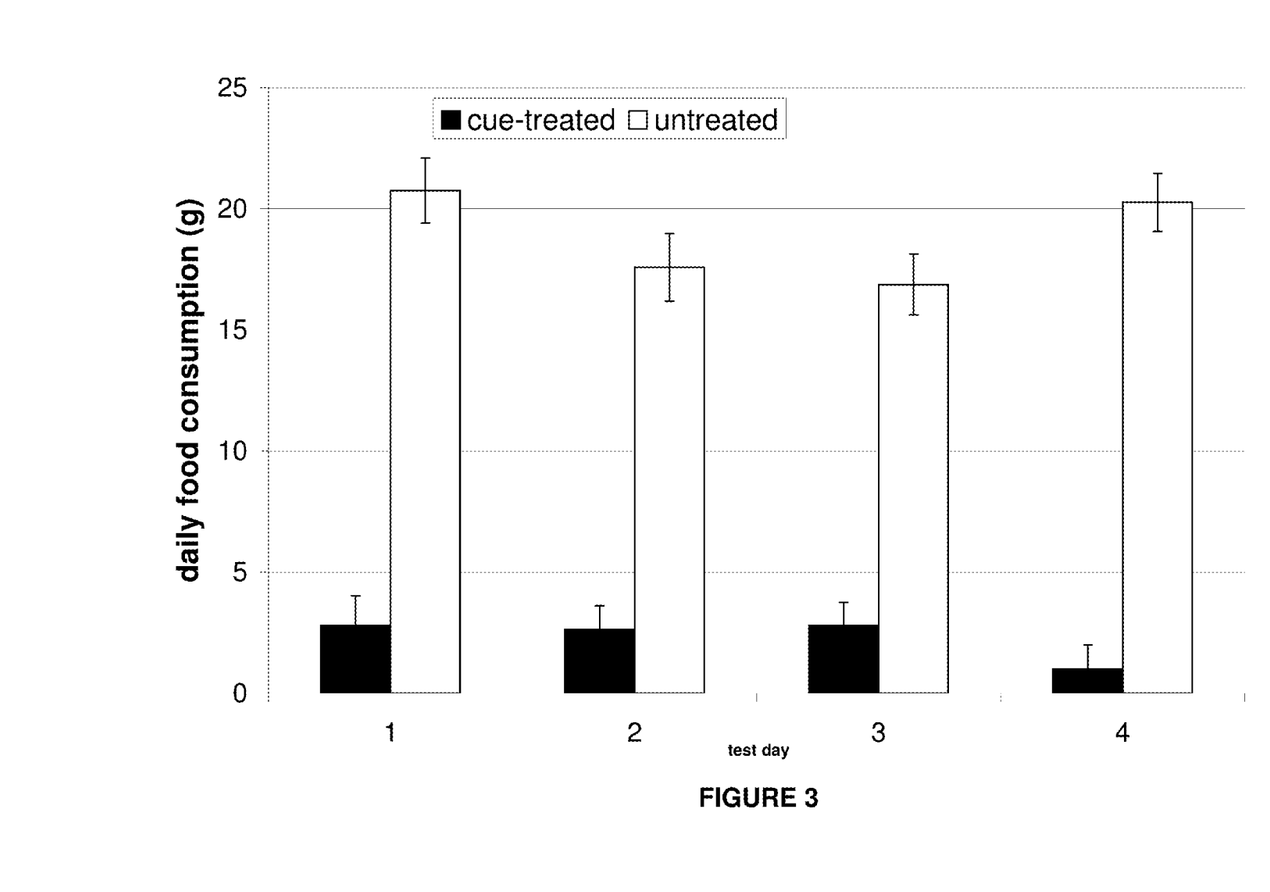
FIG. 3 illustrates preference of group-caged birds for treated (i.e., ultraviolet-absorbent cue) versus untreated food subsequent to repellent conditioning (Example 1). Consumption of treated food was significantly less than that of untreated food among 10 cages of birds (5 birds per cage) throughout the 4-day test (P<0.001).

In the final experiment, 5 experimentally-naïve red-winged blackbirds within each of 10 cages were offered two bowls of sunflower seeds treated with an ultraviolet-absorbent bird repellent (the anthroquinone, AVIPEL, ARKION Life Sciences LLC, Wilmington, Del.) during a single day of repellent conditioning. All birds were subsequently offered one bowl of sunflower seeds treated with an ultraviolet-absorbent cue (AEROXIDE P25, Evonik Goldschmidt Corp., Hopewell, Va.) and one bowl of untreated sunflower seeds. This bird repellency experiment evaluated preferences subsequent to repellent conditioning for group-caged birds. Consumption of treated food was significantly less than that of untreated food throughout the 4-day test (P<0.001; FIG. 3).

These data demonstrate that, in the absence of repellent conditioning, consumption of food treated with the UV-A- and UV-B-absorbent cue was not different than that of untreated food. Subsequent to conditioning with a UV-A- and UV-B-absorbent bird repellent, however, birds significantly avoided the ultraviolet-absorbent cue during the test of the final experiment. Thus, by using visual cue agents that exhibit spectral characteristics sufficiently similar to the previously-applied repellent treatment, the amount of the repellent agent may be significantly reduced and yet effectively repel birds.

Example 2

Figure 4:
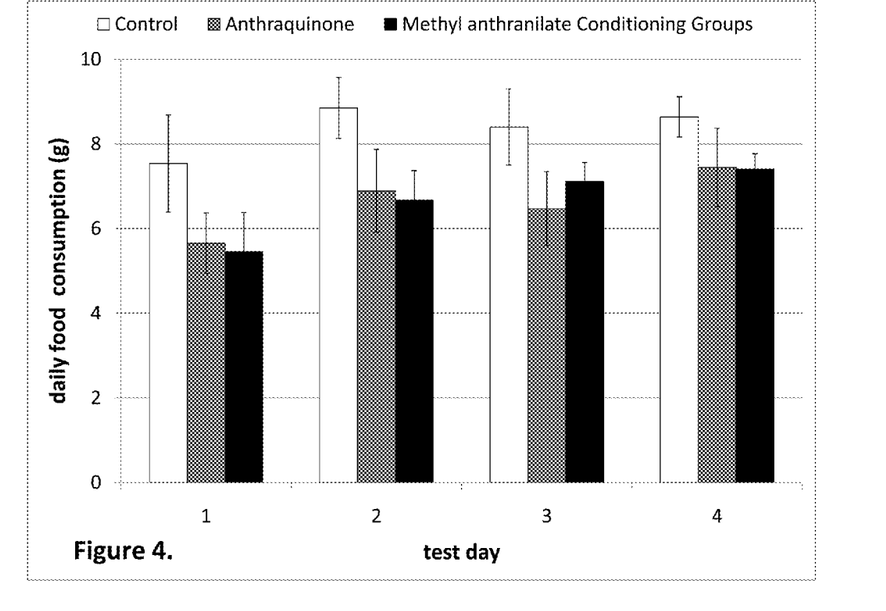

In this experiment, 35 experimentally-naïve red-winged blackbirds within individual cages were randomly assigned to 1 of 3 conditioning groups. All birds in the control group (n=13) were offered one bowl of sunflower seeds treated with an ultraviolet-absorbent cue (AEROXIDE P25, Evonik Goldschmidt Corp., Hopewell, Va.); all birds in the anthraquinone conditioning group (n=11) were offered one bowl of sunflower seeds treated with an anthraquinone-based, ultraviolet-absorbent bird repellent (AVIPEL, ARKION Life Sciences LLC, New Castle, Del.); and all birds in the methyl anthranilate conditioning group (n=11) were offered one bowl of sunflower seeds treated with an methyl anthranilate-based, ultraviolet-absorbent bird repellent (FOG FORCE, Natural Forces LLC, Davidson, N.C.) during a single day of repellent conditioning. All birds were also gavaged with 2 g of sunflower seeds treated with the AEROXIDE P25 cue (control group), the anthraquinone-based repellent (anthraquinone conditioning group), or the methyl anthranilate-based repellent (methyl anthranilate conditioning group) to ensure preingestive cue/postingestive consequence conditioning. All birds were subsequently offered one bowl of sunflower seeds treated with the ultraviolet-absorbent cue (AEROXIDE P25, Evonik Goldschmidt Corp., Hopewell, Va.) during a 4-day test. This bird repellency experiment evaluated consumption of ultraviolet-absorbent sunflower seeds subsequent to cue (i.e., control) and repellent conditioning for individually-caged birds. Sunflower consumption among birds conditioned with the anthraquinone- or methyl anthranilate-based repellents was significantly less than that exhibited among birds in the control group throughout the 4-day test (P<0.001; FIG. 4).

These data demonstrate that, in the absence of repellent conditioning, consumption of food treated with the UV-A- and UV-B-absorbent cue was not different than that of untreated food (baseline experiments). Subsequent to conditioning with a UV-A- and UV-B-absorbent bird repellent, however, birds significantly avoided the ultraviolet-absorbent cue during the test of the final experiment (Example 1). Moreover, results of Example 2 demonstrated that the ultraviolet absorbance of the bird repellents tested enabled subsequent avoidance of ultraviolet-absorbent sunflower seeds during the 4-day test (FIG. 4). Thus, by using visual cue agents that exhibit spectral characteristics sufficiently similar to the previously-applied repellent treatment, the amount of the repellent agent may be significantly reduced and yet effectively repel birds.

Example 3

A demonstrated in Example 1 and Werner et al. (2112. ibid, the contents of which are incorporated by reference herein) the ultraviolet feeding cue is not itself repellent to tested birds. This example demonstrates the synergistic repellency of the ultraviolet cue added to repellent food treatments. In this experiment, 110 experimentally-naïve red-winged blackbirds within individual cages were offered sunflower seeds treated with (a) an anthraquinone-based, ultraviolet-absorbent bird repellent (AVIPEL, ARKION Life Sciences LLC, New Castle, Del.) and an ultraviolet-absorbent cue (AEROXIDE P25, Acros Organics, Fair Lawn, N.J.; "repellent+cue") or (b) only the repellent (AVIPEL; "repellent"). All birds were offered one bowl of untreated sunflower, daily throughout a three-day pre-test. On the subsequent day, all birds in the "repellent+cue" group (N=55) received one bowl of sunflower treated with one of six concentrations of the repellent (0.02-0.5% repellent, by weight) and 0.2%, by weight, of the ultraviolet cue (n=9-10 birds per test group); all birds in the "repellent" group (N=55) received one bowl of sunflower treated only with one of six concentrations of the repellent (0.02-0.5% repellent; n=9-10 birds per test group). Food consumption was measured daily throughout the pre-test and test. Percent repellency was calculated as test consumption relative to average pre-test consumption (FIG. 5).

Example 1 demonstrated that, in the absence of the repellent, consumption of food treated with the ultraviolet cue was not different than that of untreated food (i.e., the ultraviolet cue is not itself repellent to tested birds; Werner et al. 2012). Compared to the repellency of food treated only with 0.02% or 0.035% of the repellent, the addition of 0.2% of the ultraviolet cue to these relatively low concentrations of the repellent synergistically increased repellency by 45-115% (FIG. 5). Thus, the addition of the ultraviolet cue to the repellent treatment synergistically increased the repellency of the repellent agent at relatively low repellent concentrations.

It is understood that the foregoing detailed description is given merely by way of illustration and that modifications and variations may be made therein without departing from the spirit and scope of the invention.

I claim:

1. A method for reducing an amount of anthraquinone used to repel birds from a target, the method comprising the following steps:

a. application of a first treatment comprising an anthraquinone bird repellent agent to said target in an amount effective to repel said birds, and b. application of one or more subsequent treatments comprising a visual cue agent that exhibits spectral characteristics sufficiently similar to said anthraquinone that said birds do not visually differentiate between said first treatment and said subsequent treatments, wherein said anthraquinone is applied at a significantly lower amount than said first treatment, and said visual cue agent is applied at an amount effective to be visibly recognized by said birds.

2. The method of claim 1 wherein said birds are wild birds.

3. The method of claim 1 wherein said targets comprise structures, agricultural fields or crops, seeds, seedlings, orchards, vineyards, livestock feed, fertilizers, pesticides, animal or insect baits, or combinations thereof.

4. The method of claim 3 wherein said crops comprise corn, fruit, grains, grasses, legumes, lettuce, millet, oats, rice, row crops, sorghum, sunflower, tree nuts, turf, vegetables, or wheat.

5. The method of claim 1 wherein said first treatment further comprises said visual cue agent.

6. The method of claim 1 wherein said first treatment comprises substantially none of said visual cue agent.

7. The method of claim 1 wherein said visual cue agent is selected from the group consisting of titanium (IV) oxide, trisiloxanes, and siloxanes.

8. The method of claim 1 wherein said visual cue agent comprises titanium (IV) oxide.

9. The method of claim 1 wherein said lower amount of said anthraquinone in said subsequent treatment is between about 10% to about 60% of said amount in said first treatment.

10. The method of claim 1 wherein said lower amount of said anthraquinone in said subsequent treatment is between about 25% to about 60% of said amount in said first treatment.

11. The method of claim 1 wherein said lower amount of said anthraquinone in said subsequent treatment is between about 40% to about 60% of said amount in said first treatment.

12. The method of claim 1 wherein said visual cue agent comprises titanium (IV) oxide, and said anthraquinone and said titanium (IV) oxide are provided in a synergistically effective amount in said subsequent treatment.

13. The method of claim 12 wherein said anthraquinone comprises between 0.02% to 0.035%, by weight, of said subsequent treatment and said titanium (IV) oxide comprises 0.2%, by weight, of said subsequent treatment.

14. In a method for reducing an amount of anthraquinone used to repel birds from a target comprising applying a first treatment of an anthraquinone bird repellent agent to said target in an amount effective to repel said birds, wherein the improvement comprises applying one or more subsequent treatments to said target which comprise a visual cue agent that exhibits spectral characteristics sufficiently similar to said anthraquinone that said birds do not visually differentiate between said first treatment and said subsequent treatments, wherein said anthraquinone is applied at a significantly lower amount than said first treatment, and said visual cue agent is applied at an amount effective to be visibly recognized by said birds.

* * * * *